United States Patent [19]
Milner

[11] Patent Number: 5,091,442
[45] Date of Patent: Feb. 25, 1992

[54] TUBULAR ARTICLES

[75] Inventor: Richard Milner, Bishops Stortford, United Kingdom

[73] Assignee: Smith and Nephew plc, United Kingdom

[21] Appl. No.: 613,581

[22] PCT Filed: Sep. 6, 1989

[86] PCT No.: PCT/GB89/01048
§ 371 Date: Nov. 28, 1990
§ 102(e) Date: Nov. 28, 1990

[87] PCT Pub. No.: WO90/02573
PCT Pub. Date: Mar. 22, 1990

[30] Foreign Application Priority Data

Sep. 7, 1988 [GB] United Kingdom ............... 8820945
Aug. 23, 1989 [GB] United Kingdom .. PCT/GB89/0978

[51] Int. Cl.$^5$ ....................... A61M 25/00; C08L 7/02; C08K 5/06
[52] U.S. Cl. .................................... 523/122; 604/347; 604/349
[58] Field of Search ....................... 524/190, 339, 341; 523/122

[56] References Cited

U.S. PATENT DOCUMENTS

| | | | |
|---|---|---|---|
| 4,415,548 | 11/1983 | Reddy | 604/289 |
| 4,592,920 | 6/1986 | Murtfeldt | 604/280 |
| 4,675,347 | 6/1981 | Mochizuki et al. | 523/122 |
| 4,723,950 | 2/1988 | Lee | 604/322 |
| 4,853,978 | 8/1989 | Stockum | 604/292 |
| 4,963,623 | 10/1990 | Miller et al. | 128/844 |

FOREIGN PATENT DOCUMENTS 0229862 7/1987 European Pat. Off. .
2623087 5/1989 France .

Primary Examiner—Paul R. Michl
Assistant Examiner—Peter Szekely
Attorney, Agent, or Firm—Rosenman & Colin

[57] ABSTRACT

Tubular articles such as condoms or catheters are rendered antimicrobially effective by incorporating therein an effective amount of a non-ionic sparingly water soluble antimicrobial agent. Preferably the antimicrobial is triclosan and the tubular article is a condom made from natural rubber latex. A method of manufacturing the tubular articles is described in which the anti-microbial agent is incorporated into the material forming the article before the article is formed.

14 Claims, No Drawings

TUBULAR ARTICLES

This invention relates to tubular articles such as condoms or catheters rendered antimicrobially effective by incorporating therein an effective amount of a non-ionic sparingly water soluble antimicrobial agent such as triclosan into the material such as natural rubber from which the article is made.

For many elastomeric tubular articles which are used in the medical or veterinary sciences it is often desirable to treat them so they can prevent the passage of bacteria or virus or even have a microbiocidal effect at least at their surfaces. Such articles include catheters such a urethral catheters, condoms, wound drains, endotracheal tubes and the like. Heretofore such articles have been treated with antimicrobial agents by washing with a solution of the agent or by treating it with a cream or lubricating oil or powders which contain an antimicrobial agent.

It would be useful if the aforementioned articles could be manufactured with the antimicrobial agent in situ. Unfortunately it has proved to be extremely difficult to produce articles made of rubbers such as natural rubber latex or the like incorporating an antimicrobial agent. For example, the agents have tendency to destabalise the materials from which the article is formed, for example by causing gelling of a latex. However, a method has now been discovered which allows articles to be formed which incorporate an antimicrobially effective amount of an agent which reduces the tendency for bacteria to grow on the surface of the article and then improves the barrier properties of the article against transmission of bacteria and even of viruses such as the HIV and hepatitis B virus.

The present invention provides a method for the manufacture of an antimicrobially effective tubular article which comprises including an antimicrobially effective amount of a non-ionic sparingly water soluble antimicrobial agent in an aqueous dispersion of the article material prior to forming the article.

The present invention also provides an antimicrobial tubular article which contains a non-ionic sparingly water soluble antimicrobial agent.

The antimicrobial agent is non-ionic at neutral pH values and only sparingly soluble in water. By sparingly water soluble it is meant that the antimicrobial agent has a solubility in water at 20° C. of less than 0.1 gm/liter, preferably less than 0.05 gm/liter.

The article material will contain (i.e. within its body as opposed to residing only on its surface) an antimicrobially effective amount of antimicrobial agent. Suitably the article material may contain from 0.1 to 10% w/w of antimicrobial agent, more suitably 1 to 5% w/w and preferably about 1.0% ww.

The material which forms the article can be any one of those which are conventionally used for forming such articles especially condoms and include natural rubber, polyvinyl chloride and polyurethane. The use of a natural rubber latex to form the article material is preferred. The use of a non-ionic sparingly soluble antimicrobial agent in a natural rubber latex article offers a method of overcoming many of the potential problems which could occur with natural rubber latex articles if they are susceptible to penetration by virus such as those responsible for AIDS and Hepatitis B.

From the foregoing it will be appreciated that in a preferred aspect this invention provides a natural rubber latex tubular article which contains a non-ionic, sparingly soluble antimicrobial agent.

The preferred antimicrobial agent is 2,4,4'-trichloro-2'-hydroxydiphenyl ether (triclosan).

Thus in a preferred aspect the present invention provides a natural rubber latex tubular article which contains 2,4,4'-trichloro-2'-hydroxydiphenyl ether.

These antimicrobial agents are particularly suitable for incorporation into catheters and condoms formed from natural rubber latex. It has been observed that natural rubber latices may be coagulated by ionic antimicrobial agent. If articles formed from natural rubber latices are to be treated with such antimicrobial agents in the prior art, it is only after the rubber has been vulcanised that this can be achieved. The nature of the surface of cured rubber articles is such as to be not readily coated or impregnated with for example an antimicrobial agent. Methods of overcoming this problem have included coating the article with the antimicrobial agent in a binding agent modifying the rubber surface to make it responsive to binding the antimicrobial agent or by treating the surface with a solvent to cause the rubber to swell and then impregnating with the antimicrobial agent in the same or another solvent and finally removing the solvent. These processes are difficult to carry out and do not give a consistent product. Surprisingly it has been found that non-ionic, sparingly water soluble antimicrobial agents do not coagulate natural rubber latex. This enables the antimicrobial agent to be uniformly mixed with the rubber latex in the fluid pre-cured state which makes manufacture of rubber articles made therefrom easier as it requires no post-cure operations on the article and can also provide a more consistent product. The low solubility of the antimicrobial agent means that it is not removed during the leaching step in the tubular article manufacturing process yet the antimicrobial agent is found to be effectively released from both the inside and outside of the article under conditions of which simulate wear.

Suitable non-ionic, sparingly soluble antimicrobial agents include phenol derivatives such as chlorophene, dichloroxylenol, hexachloraphane; diphenyl derivatives, halogenated hydroxy diphenyl derivatives such as diphenyl ethers for example 2,4,4'-trichloro-2'-hydroxy diphenyl ether (triclosan); and agents such as diacetylamino-azotoluene and triclocarban. The preferred antimicrobial agent is triclosan.

The articles containing antimicrobial agent may be prepared by mixing the required amount of agent with the article material, for example an aqueous dispersion such as a natural rubber latex. The agent may have been previously formed into a dispersion by mixing with a little of the latex or by mixing with water and dispersing agents. The rest of the latex may be gradually mixed with this dispersion until a homogenous mixture results. The article is then formed in the usual manner.

Thus, a former may be first dipped into a coagulant solution and allowed to dry. Thereafter the coated former is dipped into the latex, removed, dried and immersed in a leaching bath. After drying the article may then be 'cured'. Alternatively, condoms or catheters may be prepared by conventional processes not employing coagulants, for example acid gellation or heat gellation as well as multivalent cation gellation. Condoms are most aptly prepared by the conventional double dipping process.

In a process described above the antimicrobial agent may be distributed through the whole of the article material if desired so that the agent may be released from both the inside and the outside of the article. However, it may be desirable for some purposes to have the agent available only on the inside or wearer-contacting surface of the article. The agent may be present therefore in the material which forms the last coat on the former, that is becomes the inside of the article when the article is removed from the former. Thus with a condom the vaginal flora is less likely to be disturbed. Reversing the method when producing a catheter means that a product can be produced where most of the antibacterial agent can be available on the outside of the catheter.

It will be understood that in a preferred aspect this invention provides a thin polymer condom which contains 2,4,4$^1$-trichloro-2$^1$-hydroxydiphenyl ether (triclosan).

Such condoms incorporating a non-ionic sparingly water soluble antimicrobial agent offer the user a higher degree of protection from common infecting organisms that might penetrate through any discontinuity in the condom.

The present invention provides a method of reducing the risk of infection which comprises using thin polymer condom which contain 2,4,4$^1$-trichloro-2$^1$-hydroxydiphenyl ether (triclosan). The condom contains an antimicrobially effective amount of triclosan. The triclosan provides a protection for the period of use by improving the barrier property of the condom, for example with respect to HIV.

In a further preferred aspect the present invention provides a condom which contains a non-ionic, sparingly water soluble antimicrobial agent and which has at least on the inside surface thereof a powder containing triclosan.

The powder may contain an antimicrobially effective amount of triclosan. The powder may suitably contain from 0.1 to 10% w/w of triclosan, more suitably may contain from 0.5 to 8% w/w and preferably contains about 1% w/w.

The powder containing an antimicrobially effective amount of triclosan may be obtained by methods which comprise mixing of the ingredients. Suitable methods include (a) mixing a solution of triclosan in acetone with the powder, drying, grinding and sieving the resulting powder to remove large particles and (b) mixing the dry powders together.

The powder containing triclosan may be coated onto the inside of the condom incorporating the non-ionic, sparingly water soluble antimicrobial agent such as triclosan itself in the way lubricating powders are conventionally applied.

The article according to this invention may also contain a further antibacterial agent is desired, for example chlorhexidine digluconate.

The following examples illustrate the invention.

EXAMPLE 1

A condom former of glass is thoroughly washed using dilute acid or alkali solutions. The former is rinsed in soft water and dried. The former is dipped into the natural rubber latex. The former is removed and the latex coating dried and evenly distributed over the former by rotation and agitation of the former. The former is then dipped a second time into the latex since a second layer of latex reduces the chance of any pin-holes remaining in the final product. The former is removed and the second coat dried. The article is then leached in a tank of warm water at 70° C. for two minutes. After leaching the former is dipped in an aqueous solution containing 10% w/w of chlorhexidine digluconate for 20 seconds and then removed and shaken to remove any adhering water droplets.

The rubber latex contained 1% by weight of triclosan. This was prepared as follows:

The hydroxy halogenated biphenyl ether 2,4,4$^1$-trichloro-2$^1$-hydroxy diphenyl ether (triclosan) was incorporated into a natural rubber latex by mixing triclosan (21 g) with a small quantity of latex to form a paste. The latex was gradually diluted with more latex until the required concentration was achieved. The final latex formulation was:
Latex (42%) 4940 g
Triclosan 21 g

EXAMPLE 2

The procedure of Example 1 was repeated omitting the chlorhexidine step.

EXAMPLE 3

The procedure of Example 2 was repeated but the triclosan was incorporated into the first latex only.

EXAMPLE 4

A catheter is prepared by a multiple dipping process whereby a former of appropriate size is repeatedly dipped in a bath of pre-vulcanised rubber latex to build up layers of rubber to give the required wall thickness. The final latex dip incorporated 1% triclosan (based on solids content of latex).

I claim:

1. A method for the manufacture of an antimicrobially effective tubular article which comprises including an antimicrobially effective amount of a non-ionic sparingly water soluble antimicrobial agent in an aqueous dispersion of the article material prior to forming the article.

2. A tubular article produced by the inclusion of an antimicrobially effective amount of a non-ionic sparingly water soluble antimicrobial agent in an aqueous dispersion of the article material prior to forming the article.

3. A method as claimed in claim 1 wherein the antimicrobial agent is 2,4,4$^1$-trichloro-2$^1$-hydroxydiphenyl ether.

4. A method as claimed in claim 3 wherein the article is a condom.

5. A method as claimed in claim 3 wherein the article is a catheter.

6. A method as claimed in claim 1 wherein the material is a natural rubber latex.

7. An article as claimed in claim 2 wherein the antimicrobial agent is 2,4,4$^1$-trichloro-2$^1$-hydroxydiphenyl ether.

8. An article as claimed in claim 7 which is a condom.

9. An article as claimed in claim 8 which is a catheter.

10. An article as claimed in claim 2 wherein the material is natural rubber.

11. A method as claimed in claim 1, wherein an antimicrobially effective amount of 2,4,4'-trichloro-2'-hydroxydiphenyl ether is included in a natural rubber latex, which is thereafter formed into a condom.

12. A method as claimed in claim 1, wherein an antimicrobially effective amount of 2,4,4'-trichloro-2'-hydroxydiphenyl ether is included in a natural rubber latex, which is thereafter formed into a catheter.

13. An article as claimed in claim 2, wherein said antimicrobial agent is 2,4,4'-trichloro-2'-hydroxydiphenyl ether, said aqueous dispersion is a natural rubber latex and said article is a condom.

14. An article as claimed in claim 2, wherein said antimicrobial agent is 2,4,4'-trichloro-2'-hydroxydiphenyl ether, said aqueous dispersion is a natural rubber latex and said article is a catheter.

* * * * *